United States Patent [19]

Shozda

[11] 3,954,936
[45] May 4, 1976

[54] O-NITROSOPHENOLS AS EXTRACTANTS FOR METAL VALUES

[75] Inventor: Raymond John Shozda, Landenberg, Pa.

[73] Assignee: E. I. Du Pont de Nemours and Company, Wilmington, Del.

[22] Filed: Jan. 29, 1973

[21] Appl. No.: 327,661

[52] U.S. Cl. ............................ 423/24; 423/49; 423/139; 260/621 N
[51] Int. Cl.$^2$ .................. C01G 3/00; C01G 45/00; C01G 51/00; C01G 53/00
[58] Field of Search ............ 260/622, 619 R, 621 R, 260/621 N; 423/139, 49, 24; 75/101 BE

[56] References Cited
UNITED STATES PATENTS

| | | | |
|---|---|---|---|
| 3,428,449 | 2/1969 | Swanson | 423/24 X |
| 3,637,711 | 1/1972 | Budde et al. | 423/24 X |
| 3,655,347 | 4/1972 | Mattison et al. | 423/24 X |
| 3,770,834 | 11/1973 | Prosser | 260/621 N |
| 3,848,002 | 11/1974 | Weis et al. | 260/621 N |

FOREIGN PATENTS OR APPLICATIONS

| | | | |
|---|---|---|---|
| 2,091,794 | 1/1972 | France | 75/101 BE |

OTHER PUBLICATIONS

Cronheim, *Industrial & Engineering Chemistry, Analytical Edition,* Vol. 14, (1942), pp. 445–448.
Cronheim, *Journal of Organic Chemistry,* Vol. 12, (1947), pp. 1–19.

*Primary Examiner*—Oscar R. Vertiz
*Assistant Examiner*—Brian E. Hearn

[57] ABSTRACT o-Nitrosophenols adapted for the liquid-liquid extraction of metals, e.g., copper, from aqueous solutions and a nitrosation process for the preparation of the phenols.

3 Claims, No Drawings

3,954,936

O-NITROSOPHENOLS AS EXTRACTANTS FOR METAL VALUES

SUMMARY OF THE INVENTION

A compound especially adapted to remove metal ions, e.g., $Cu^{++}$ from an aqueous solution which compound has the formula

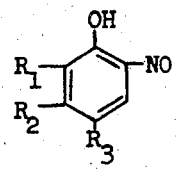

wherein the substituents $R_1$, $R_2$ and $R_3$ are selected from the class consisting of alkyl, alkoxy, aralkyl, alkenyl and aralkenyl. At least one of said substituents contains carbon atoms; the remaining groups are additionally selected from the class consisting of hydrogen and electronegative groups such as chlorine, nitro- and sulfoamide groups of the formula

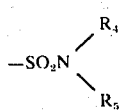

wherein $R_4$ and $R_5$ are lower alkyl groups. The compound is further characterized in that the total number of carbon atoms on the substituent groups is 6–20 including the carbon atoms on the sulfamide group. In preferred compounds, $R_2$ is hydrogen and $R_3$ or $R_1$ is an alkyl group having 8–12 carbon atoms with the remaining group being chlorine.

A novel process for the preparation of a metallic complex of a substituted orthonitrosophenol which comprises contacting a substituted phenol, e.g., o-chloro-p-(t-octyl)phenol with a nitrosating compound, e.g., sodium nitrite, in the presence of a mixed solvent consisting essentially of water and an organic solvent, preferably a hydroxyl-containing compound, e.g., ethanol, at an initial pH of at least 5.0 and preferably 5.2–5.8 at a temperature in the range 20°–150°C. and preferably 25°–60°C. in the presence of a metallic ion, e.g., $Cu^{++}$.

DESCRIPTION OF THE PRIOR ART

The selective removal of metal values from aqueous streams with organic extractants, e.g., the α-hydroxyoximes, has been shown in the literature. U.S. Pat. No. 3,224,873, issued on Dec. 21, 1965 describes the liquid-liquid extraction of copper values using an α-hydroxyoxime in an organic solvent and recovery of copper from the organic phase. U.S. Pat. No. 3,426,449, issued on Feb. 18, 1969, discloses the use of phenolic oximes in a similar liquid-liquid extraction. The above-mentioned oximes complex with the metallic ions in the aqueous phase and then transfer them to the organic phase, following which the metal values are recovered from the organic phase. It has now been discovered that certain new o-nitrosophenols function in a manner similar to the above-described oximes. Several possible procedures for o-nitrosation of simple phenols have been disclosed. One procedure reported by K. Maruyama and I. Tanimoto in the *Bulletin of the Chemical Society of Japan*, Vol. 44, pages 3120–3123 (1971) involves the use of hydroxylamine and hydrogen peroxide as the nitrosating system. However, such a method fails to give detectable amounts of nitrosophenol with phenols having bulky substituents, for example p-(t-butyl)phenol. It has been disclosed that simple phenols can be nitrosated by first isolating the nitrosation product as a copper complex as reported by G. Cronheim in the *Journal of Organic Chemistry*, Vol. 12, pages 1–29 (1947) and J. Charalambous et al. in the *Journal of the Chemical Society*, (A), pages 2787–91 (1969) and (A) pages 602–605 (1971) but of the alkyl substituents proposed, none has more than five carbon atoms. These particular nitrosophenols were observed to form strongly colored inner complex salts with heavy metals. However, it has been discovered that the disclosed compounds are too soluble in water to permit their use in a liquid-liquid extraction in the manner in which the oximes are employed. Attempts to prepare o-nitrosophenols with higher alkyl groups to reduce water solubility and enhance solubility in an organic solvent following the prior art procedures described hereinabove gave considerable difficulty. Although simple phenols can be nitrosated with cold sulfuric acid or hydrochloric acid and sodium nitrite, p-(t-octyl)phenol and p-(t-butyl)phenol failed to yield a measurable amount of nitrosation product. Likewise contacting p-(t-butyl)phenol with hydroxyl amine and hydrogen peroxide in aqueous alcohol and alcoholic media failed to yield detectable amounts of the nitrosation product.

DESCRIPTION OF PREFERRED EMBODIMENTS

The starting materials for the present invention are phenols having the formula

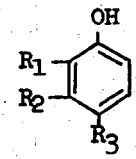

wherein the total number of carbon atoms in the substituent groups are 6–20 and preferably 8–12. At least one of the substituent groups is carbon containing and is either alkyl, alkoxy, aralkyl, alkenyl or aralkenyl group while the remaining groups may be one of the above-described groups, or in addition can be hydrogen, hydroxyl, halogen, especially chlorine, nitro and sulfoamide groups having the formula

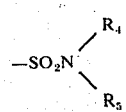

wherein $R_4$ and $R_5$ are either hydrogen or lower alkyl groups provided that the total number of carbon atoms in the substituent groups does not exceed that set forth hereinabove. Such phenols include but are not limited to the alkyl substituted phenols such as octyl phenols, e.g., 2-chloro-4-(t-octyl)phenol; nonyl phenols, e.g. 4-nonylphenol; dodecylphenols, e.g., 2-chloro-4-dodecylphenol; hexylphenols, e.g. 2-chloro-4-hexylphenol, 2-nitro-4-hexylphenol, 2,3 or 4-(eicosyl)-phenol, and the disubstituted compounds such as 2,3- di-(decyl)phenol, 2,4-di-(decyl)phenol, 2-chloro-3,4-di-(decyl)phenol, 2,3,4-tri(hexyl)phenol, 3-chloro-2,4-di-(hexyl)phenol. Examples of compounds also included are dodecyl phenol, 2-chloro-4-styrylphenol, β-methyl styrylphenol, dodecyl benzylphenol, 2-(N,N-diethyl sulfonamido)-4-octylphenol, 4-cetyloxyphenol, 2-chloro-4-cetyloxyphenol, 2-benzyl-4-octylphenol, 2dodecanoyl-4-phenylphenol, 6-octylresorcinol, 3 or 4-octyloxyphenol and 4-chlorol-2-dodecenylphenol. Additional compounds are obvious to those skilled in the art as is the fact that the difficulty in preparing substituted compounds increases depending upon the number, position and size of the substituent groups.

The phenols having the formula

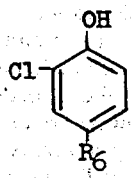

wherein $R_6$ is an alkyl group having 8–12 carbon atoms are preferred because of the extraction efficiency of the resultant o-nitrosophenol and because the addition of chlorine improves the ability of the o-nitrosophenol to reject iron. The phenol starting material can be present at a concentration in the organic phase of about 5–50% and preferably 10–30% by weight based upon the total weight of the organic phase.

An important feature of the present invention is the employment of a mixed solvent for nitrosation. The water phase maintains the inorganics involved in the reaction in solution and enhances the degree of nitrosation while the organic phase maintains the starting material in solution. The mixed solvent consists essentially of water and watermiscible organic solvent, e.g., a hydroxyl compound having less than about 8 carbon atoms which is stable at the reaction conditions in the presenece of the phenolic compound and the metallic ion. Suitable hydroxy-containing compounds include the lower organic alcohols, e.g., methanol, butanol and 2-ethoxy ethanols, preferably alcohols having 1–5 carbon atoms, especially ethanol; and glycols such as ethylene glycol. Other suitable solvents include dioxane and dimethyl sulfoxide. The volume ratio of water to the hydroxyl-containing compounds is usually in the range of 1/0.5 to 1/4, and preferably is in the range 1/1.5 to 1/2.

Nitrosating agents which are known to those skilled in the art are operable in the present process provided they are stable in the reaciton medium. The preferred nitrosating agents are the alkali metal nitrites especially sodium nitrite. Other nitrosating agents include soluble inorganic nitrites such as alkali earth metal, transition metal and Group 8 metal nitrites, and the hydrolytically stable organic nitrites such as the alkyl nitrites having 1–6 carbon atoms, e.g., ethyl nitrite, propyl nitrite, butyl nitrite, amyl nitrite and isoamyl nitrite. The concentration of nitrosating agent is usually 10–50% and preferably 15–40% by weight based upon the total weight of water provided that at least one and preferably 2–4 moles of agent are present per mole of the phenol starting material.

Divalent metallic ions which have been shown to be operable to produce the o-nitrosophenol include ions of copper, nickel and mercury although other ions which readily complex to produce the nitrosophenol are within the purview of the present invention. The cupric ion is preferred. Preferably the metallic ion is present at an equivalent concentration with the phenol.

The process of the present invention can be conducted over a wide range of temperatures, for example, from 20°–150°C. depending upon the stability of the selected reactants. The preferred temperature range for the practice of the present invention is 25°–60°C. which range provides a reasonably rapid reaction with minimum degradation of reactants. The time of reaction is usually more than two hours and generally in the range 4–6 hours with shorter times being employed at elevated temperatures.

The initial pH of the reaction medium is a critical consideration in the present process because the yield of the nitrosophenol is dependent upon that pH. It is preferred to employ a pH of at least 5.0 and usually 5.2–6.0 and preferably 5.2–5.8. The optimum pH for a given reaction will vary slightly depending upon the solvent, the acidity of the phenol and the nitrosating agent but will fall within the aforementioned ranges. Buffer systems known to one skilled in the art are employed to produce the indicated pH. Examples of operable buffer systems include but are not limited to tartaric acid/sodium hydroxide, citric acid/disodium phosphate, monosodium citrate, potassium acid phthalate/sodium hydroxide.

In addition to the extraction of copper as set forth in the following examples, the o-nitrosophenols of the present invention can extract other metals such as cobalt, manganese and nickel.

In an industrial scale process, a solution of the o-nitrosophenol in substantially water-immiscible organic solvent, e.g., aliphatic or aromatic hydrocarbons such as benzene, toluene, xylene and kerosene or chloroform would be countercurrently contacted with an aqueous stream containing the metal values. Suitable aqueous streams are obtained, for example, by leaching metal containing ore with water assisted by bacteria. The metal is selectively transferred to the organic phase and bound as a complex with the o-nitosophenol. The metal is then freed from the complex by contacting it with acid to produce an acid stream containing a high concentration of metal. The metal values can then be recovered by known procedures.

The following examples are presented to illustrate but not to restrict the present invention. Parts and percentages are by weight unless otherwise specified.

EXAMPLE 1

A three-neck, 250 ml. flask fitted with a thermometer, a pH electrode, magnetic stirring rod and a condenser which was vented to a bubbler system was charged with 3.2 g. $CuSO_4 \cdot 5H_2O$, 25 ml. water, 12.7 g. potassium acetate, 6.0 g. of o-chloro-p-(t-octyl)phenol, and 38 ml. of absolute ethanol. Approximately 17 ml. of glacial acetic acid were then added to bring the pH of the system to 5.65 following which 4.3 g. sodium nitrite were introduced. The system was closed to the venting bubbler, heated rapidly with stirring to bring the temperature of the contents of the flask to 50°C., and maintained at 50°C. for 5 hours. Solids were produced during the reaction.

After the reaction period, the mixture was cooled to about room temperature and poured over ice. The resulting mixture was extracted with several portions of ether which portions totaled about 350 ml. The extract containing dissolved and suspended product was washed four times with 100 ml. portions of water to remove soluble materials. The washed extract was then dried over sodium sulfate and then decanted through a paper filter. The sodium sulfate was washed repeatedly with small portions of ether until it was substantially white and the washes were decanted onto the filter. The dry weight of purple solid product amounted to 3.5 g. of the copper complex of 2-nitroso-4-(t-octyl)-6-chlorophenol. Its purity as determined by analysis for copper was 95.5%. The filtrate yielded an additional 3.7 g. of purple material which contained 34% by weight of the o-nitrosophenol copper complex as determined by analysis for copper. The total yield of copper complex in both fractions amounted to 4.6 g. or approximately 61.5% of the theoretical amount.

Approximately 3.3 g. of solid product produced was dissolved in chloroform and shaken successively with 25 ml. portions of sulfuric acid (20%). The organic solution was washed with distilled water until the wash was neutral to test paper. The organic solution was then dried with sodium sulfate. Removal of the solvent left 2.84 g. of a viscous liquid which was 2-nitroso-4-(t-octyl)-6-chlorophenol of 95.5% purity. The clear viscous product was dissolved in 100 ml. of chloroform and then divided in 25 ml. portions. Each of three of the portions were added to three 25 ml. portions of an aqueous solution of copper sulfate having the pH (adjusted by the addition of sulfuric acid) and concentration set forth in Table I. The mixtures were shaken for 20 minutes at room temperature and then permitted to separate. The pH of the aqueous layers were measured and the layers were analyzed for copper by absorption spectroscopy. Distribution coefficients were calculated from the equation $$D = \frac{\text{Concentration of copper in the organic phase}}{\text{Concentration of Copper in the aqueous phase}}$$

TABLE I

| SAMPLE | A | B | C |
|---|---|---|---|
| Initial pH | 1.5 | 2.35 | 3.25 |
| Equilibrium pH | 1.25 | 1.50 | 1.50 |
| Initial Copper in Aqueous Phase (ppm) | 3280 | 3220 | 3100 |
| Equilibrium Copper in Aqueous Phase (ppm)- | 1585 | 1170 | 1125 |
| Organic Phase (ppm) | 1695 | 2050 | 1975 |
| D | 1.07 | 1.75 | 1.75 |

Hydrated nickel sulfate or mercury acetate can be substituted for the foregoing copper sulfate and p-t-octyl)-nitrosophenol can be employed as the starting phenol.

EXAMPLES 2–5

The procedure of Example 1 was repeated except that 6.3 grams of $CuSO_4 \cdot 5H_2O$ were charged to the reactor and the amount of acetic acid and potassium acetate were varied to vary the initial pH. The results are given in Table II below.

TABLE II

| EXAMPLE | INITIAL pH | YIELD OF COPPER COMPLEX *(%) |
|---|---|---|
| 2 | 5.1 | 39 |
| 3 | 5.4 | 42 |
| 4 | 5.8 | 44 |
| 5 | 6.5 | 28 |

*By analysis of copper content of the complex

The foregoing demonstrates that there is an optimum pH with respect to yield of the complex for any given system.

EXAMPLES 6–8

The procedure of Examples 2–5 was repeated except that 6.3 grams of butyl nitrite and 6.4 grams of 2-chloro-4-nonylphenol were substituted for the respective nitrite and phenol of Examples 2–5. The results are shown in Table III.

TABLE III

| EXAMPLE | INITIAL pH | YIELD OF COPPER COMPLEX (%) |
|---|---|---|
| 6 | 5.0 | 31.5 |
| 7 | 5.6 | 38 |
| 8 | 6.15 | 28 |

EXAMPLES 9–15

Example 1 was repeated except that 38 ml. of the solvent shown in the following table was substituted for ethanol with the indicated result.

| EXAMPLE | SOLVENT | YIELD (%) |
|---|---|---|
| 9 | 2-ethoxyethanol | 52.5 |
| 10 | p-dioxane | 18.9 |
| 11 | 2-propanol | 54.8 |
| 12 | 1,2-dimethoxyethane | 32.3 |
| 13 | ethylene glycol | 33 |
| 14 | dimethyl sulfoxide | 52 |
| 15 | 2-(2-ethoxyethoxy)ethanol | 39.8 |

Although the compounds of the present invention are referred to as o-nitrosophenols, the tautomeric forms, i.e., those referred to as o-quinone monooximes are included in the scope of this invention, c.f. *Chemistry of Carbon Compounds*, E. H. Rodd, Ed., Vol. 3A Elservier Pub. Co., 1954, p. 446–447.

What is claimed is:

1. A process for recovering at least one metal value selected from the group consisting of copper, cobalt, manganese and nickel from an aqueous solution while rejecting iron comprising contacting said aqueous solution at acid pH with an organic phase comprising a liquid, substantially water-immiscible, organic solvent and a substituted 6-chloro orthonitrosophenol wherein the substituent groups on said phenol contain 6–20 carbon atoms to extract at least a portion of the metal values in said aqueous solution and thereafter separating the organic phase from the aqueous phase and recovering metal values from the organic phase.

2. The process of claim 1 wherein said orthonitrosophenol has the formula

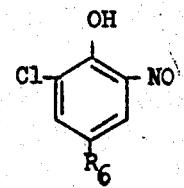

wherein $R_6$ is an alkyl group having 8–12 carbon atoms.

3. The process of claim 2 wherein said metal values consist essentially of copper in the form of the cupric ion.

* * * * *